United States Patent [19]

Matschke

[11] Patent Number: 4,699,881

[45] Date of Patent: Oct. 13, 1987

[54] CHAMBER FOR THE TREATMENT OF CELLS IN AN ELECTRIC FIELD

[75] Inventor: Christian Matschke, Alsdorf, Fed. Rep. of Germany

[73] Assignee: Kernforschungsanlage Julich Gesellschaft mit beschrankter Haftung, Julich, Fed. Rep. of Germany

[21] Appl. No.: 870,636

[22] Filed: Jun. 4, 1986

[30] Foreign Application Priority Data

Jun. 12, 1985 [DE] Fed. Rep. of Germany ....... 3521034
Jun. 25, 1985 [DE] Fed. Rep. of Germany ....... 3522610

[51] Int. Cl.$^4$ .................... C12P 17/00; G01N 27/28
[52] U.S. Cl. .................................. 435/173; 435/287; 435/289; 435/817; 204/272
[58] Field of Search .............. 435/173, 817, 287, 289; 204/272

[56] References Cited

U.S. PATENT DOCUMENTS

| | | | |
|---|---|---|---|
| 2,440,472 | 4/1948 | Horner et al. | 435/173 X |
| 2,955,076 | 10/1960 | Gosshing | 435/287 X |
| 3,095,359 | 6/1963 | Heller | 435/287 X |
| 3,133,003 | 5/1964 | Schaefer et al. | 435/287 X |
| 3,528,905 | 9/1970 | Miller | 204/272 |
| 4,578,168 | 3/1986 | Hofmann | 204/272 X |

Primary Examiner—Larry Jones
Attorney, Agent, or Firm—Karl F. Ross; Herbert Dubno

[57] ABSTRACT

The chamber for treating cells in an electric field includes an interior space for a cell suspension having a region between the electrodes inside of which the cells are exposed to the electric field. In order to provide an improved chamber the region in which the cells are treated—up to an inlet or outlet for the cell suspension—is bounded by surfaces of the electrodes which are positioned equidistant from each other. Preferable these electrode surfaces are coaxial or concentric. In one specific embodiment of my chamber a first electrode is the inner electrode and a second electrode is the outer electrode and the surfaces of the inner electrode and the inside surfaces of the outer electrode are cylindrical so that the region between the electrodes is a cylindrical annular space. The front end of the circular space opens to the exterior while the other opposing end of the circular space opens into an axial duct in the inner electrode which is connected to the inlet of the chamber by a conical passage which widens toward the exterior whose dimensions are selected so that a standard pipette can be inserted into it.

15 Claims, 4 Drawing Figures

CHAMBER FOR THE TREATMENT OF CELLS IN AN ELECTRIC FIELD

FIELD OF THE INVENTION

My present invention relates to an apparatus for the treatment of biological cells with an electric field.

BACKGROUND OF THE INVENTION

Cells can be treated with an electric field in an interior space having a region between two electrodes and receiving a suspension of cells. The cells are exposed to an electric field developed between the electrodes.

A chamber for the treatment of cells with an electric field has been taught in German Patent Document-Open Application DE-OS No. 33 17 415. In this known chamber the space provided for receiving the suspension of cells is formed by a cylindrical shaped inner body and an exterior body surrounding it. Both electrodes are wrapped around the inner body in the shape of a multiple-thread screw so that the region inside of which the cells are treated with the electric field is likewise helicoidal in shape.

In this chamber a very large number of cells simultaneously can undergo treatment by the electric field. However there is a disadvantage since not all of the cells in the region in which the treatment occurs are exposed to the same electric field strength. This increases the variations occurring in the desired product conditioned by the natural distribution of the properties of a cell population. Moreover this chamber is expensive to manufacture.

Another chamber for treating cells with an electric field is described in German Patent Document-Open Application DE-OS 33 21 239. This comprises a base plate with an additional component forming the interior space for the cell suspension and two wire shaped electrodes which project into that space. Of course the chamber is easily manufactured and economical. However the same disadvantage exists as in the previously described known chamber—that is, individual cells may not be exposed to exactly the same electric field strength in the region lying between the electrodes.

Chambers of the above described kind and those with which the invention is concerned can be used for the treatment of cells in an electric field, particularly for the fusion of cells.

One process for fusion of cells is taught in Biochimica et Biophysica Acta, 694 (1982), 227–277 (Electric Field-Mediated Fusion and Related Electrical Phenomena, U. Zimmermann). In this known process — whose course can be observed under a microscope—a membrane contact between at least two cells is induced by application of a weak alternating uniform electric field.

By the electric field dipoles induced by the polarization, processes in the cells are initiated which cause them to approach one another by their mutual attraction during their random motions through the electrical field (dielectrophoresis).

According to the structure of the cell aggregates or rows the disruption of the membrane structure between adjacent cells is triggered by an electrical rupturing pulsation. (J. Membrane Biol. 67, 165-182 (1982), U. Zimmerman and J. Vienken).

Thus—according to the current concept—holes are produced in the areas of contact of the membranes of adjacent cells which lead to a cytoplasmic continuum between both the cells and to bridge formation of lipids between the membranes of the adjacent cells. The lipid molecule is no longer associated with its original membrane. As soon as a bridge has formed, on the basis of energy considerations a common membrane structure comprising the cells connected with each other by the lipid bridges is formed to restore the lower energy curvature.

OBJECTS OF THE INVENTION

It is an object of my invention to provide an improved apparatus, particularly a chamber, for treatment of cells in an electrical field.

It is also an object of my invention to provide an improved chamber for treatment of cells in an electrical field which is easily manipulated and simple to manufacture.

It is another object of my invention to provide an improved chamber for treatment of cells in an electrical field in which individual cells are not subjected to a nonuniform electric field or to different electric field strengths.

SUMMARY OF THE INVENTION

These objects and others which will become more readily apparent hereinafter are attained in a chamber for treatment of cells comprising two electrodes which have a constant spacing from each other in a region of an interior space accessible from the outside to the suspension containing the cells.

According to my invention the region in which cells are treated with the electric field is bounded by spacedly juxtaposed concave and convex surfaces of electrodes which are equidistant from each other and which have a common cross section plane intersecting the surfaces along generally circular arc segments having a common center in this plane. Preferably these surfaces are positioned coaxially or concentrically. The region is spatially bounded by the electrodes. In all parts of the region, since it is surrounded and defined by surfaces of electrodes which are equidistant from each other, the electric field strength is equal so that all cells found in this region are subjected to the same electrical conditions.

In a first embodiment of the chamber according to my invention in the vicinity of the region in which the cells are treated the first inner electrode has a substantially cylindrical surface and the inside of the second outer electrode has an approximately cylindrical surface so that the region in which the cells are treated is an approximately cylindrical annular space. The shape of this annular space need not be circular, that is, the cross section does not need to be exactly circular but for example can also be oval, although a circular section is preferred.

In this embodiment a front end of the annular space can be open to the exterior and at its other opposing end at least one radial transverse passage in the inner electrode can connect it with an axial duct which is formed in the inner electrode. Also the end of the chamber opposite to the outlet is open to the exterior.

For the electrical treatment of the cells in an electric field the cell suspension is forced into the region where it is to be treated through the axial duct where it—with a typical electrode spacing of from 20 to 500 microns or micrometers—remains without dropping out by capillary retention. After electric treatment the cell suspension can be forced out of the region by pressurized gas (air), feeding in a second solution or by centrifugation.

In order to be able to easily connect both electrodes to an electrical power supply or source of EMF in the first embodiment of the chamber according to my invention both electrodes outside of the vicinity of the annular space are separated from each other by an insulating member which extends to the transverse passage, surrounds a part of the inner electrode near the axial duct and separates both electrodes until it reaches the outside of the chamber so that the outer electrode substantially in the vicinity of the circular space and the inner electrode in the remaining portion of the chamber are accessible from the outside. The electrical connection to the chamber can be made in this example in an easy way from the outside, whereby a connection to an electronic or electrical device for applying an alternating electric field and a device for applying a voltage pulse for performing fusion of the cells in a conventional way is made.

The axial duct in the inner electrode advantageously opens into a conical passage widening to the exterior whose dimensions are so selected that a standard pipette can be inserted therein.

With the pipette an adjustable known quantity of the cell suspension or any solution can be fed into the region where the cells are to be treated. This allows the chamber and its contents to be easily manipulated. Thus in a very simple way a plurality of chambers can be used to perform a series of treatments on cells, for example a complete series of experiments on one or more cell suspensions or alignots of a single cell suspension.

In order to be able to insert the chamber easily into an electric socket which provides contact with the electric power supply it is particularly appropriate to conically taper the outer electrode at the outlet end of the annular space.

Alternatively the first electrode is formed as an inner electrode and in the vicinity of the region where the cells are treated is substantially ball shaped (generally spheroidal) and the second electrode is formed as the outer electrode and has an inner surface in the vicinity of the region where the cells are treated which is correspondingly ball shaped so that the region is at least partially bounded or lies between two concentric substantially ball shaped surfaces.

The first electrode formed as the inner electrode is advantageously rod shaped with a ball shaped end. This inner electrode projects into an outer casing shaped like a test tube and the inner surface of the outer casing simultaneously provides the inner surface of the outer electrode.

For preparation for the electrical treatment of the cells the inner electrode is mounted in the test tube shaped outer casing and then the cell suspension or a solution and a subsequently introduced small amount of cell suspension are fed into the chamber. When the amount of solution added to the chamber is larger than the volume of the region in which the cells are to be treated the cells are caused to collect by sedimentation in the region before electrical treatment is commenced.

For guiding the inner electrode into the test tube shaped outer casing guide rings are provided on the inside of the cylindrical portion of the test tube shaped outer casing.

In order to be able to make electrical contact to the outer electrode from the outside the outer casing is formed in the vicinity of the region where the cells are treated by the outer electrode. The outer electrode can be separated from the remaining part of the outer casing by an insulating member. Alternatively the remaining part of the outer jacket can also comprise an electrical insulating body. The second electrical contact is made on the rod shaped part of the inner electrode.

Advantageously on the end opposite to the ball shaped end of the inner electrode a cap is mounted for the test tube shaped outer casing.

For the case where the outer casing in the region where the cells are treated is formed by the outer electrode and the remaining part of the outer casing comprises an electrical insulating member the cap is composed of a metal so that the electric voltage can be applied to the inner electrode through the metal cap.

For easy handling of the chamber an opening in the cap is provided with a stopper. The cell suspension is filled through this opening. For withdrawing the cell suspension after the treatment has taken place the cap is removed from the test tube shaped outer casing and with it the inner electrode. Any additional treatment of the cell suspension occurs then as usual in the test tube.

The scope of my invention can be expanded and a coupling for a pipette can be provided in one example of the first embodiment of a chamber according to my invention. This example is particularly characterized by a region where cells are treated having an outlet open to the exterior and that region at least in the vicinity of the outlet is so dimensioned that the cell suspension is held in the region. The region has an inlet which is connected with a coupling for a pipette or the like.

The chamber in the vicinity of the outlet can be shaped like a capillary tube.

In this embodiment of the chamber according to my invention the region can have a variety of shapes. Only the inlet with the coupling for a pipette and the outlet open to the exterior and the capillary dimensions are predetermined. Thus the region where the cells are treated in the chamber can be formed as is described in German Patent Document-Open Application DE-OS 33 17 415 or DE-OS 33 21 239.

Also for example in the second embodiment of the chamber according to my invention a test tube shaped outer casing can be provided which has a capillary tube at its bottom and on the cap of this chamber or on its opening an additional structure for coupling to a pipette is provided. This version of the chamber can be filled then by a pipette and emptied by forcing in a second solution (likewise by pipette).

In filling the chamber or the region containing the cell suspension the cell suspension is forced into the chamber or region of it through the coupling to the pipette or the like and for emptying the chamber or region the suspension is forced out. This process permits a particularly easy handling of the fusion chamber.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
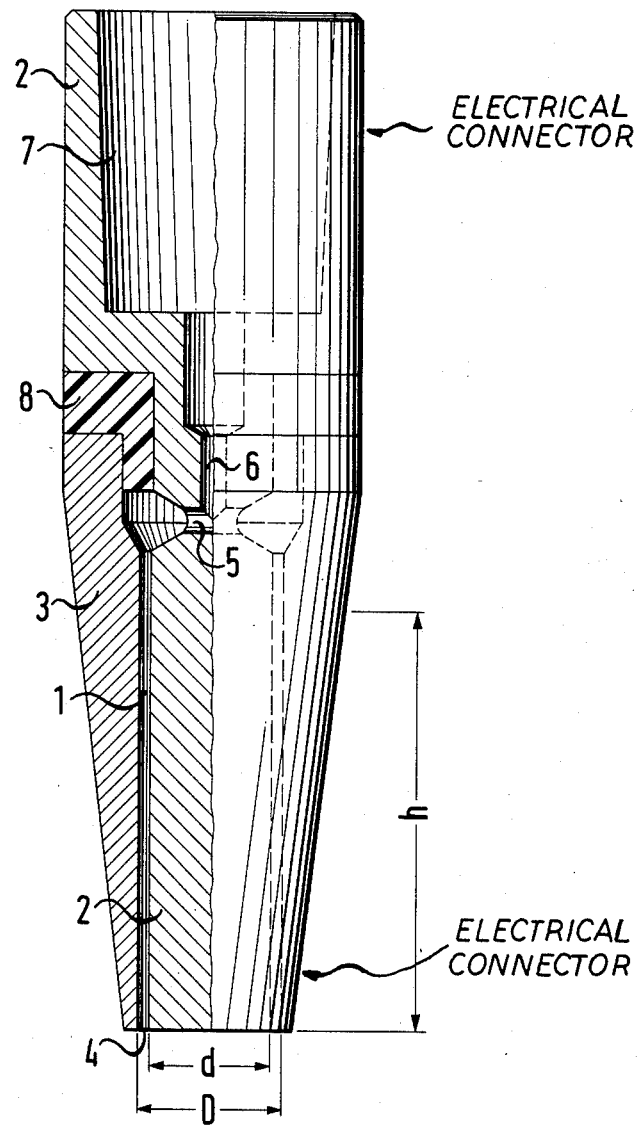
FIG. 1 is a vertical cross sectional view of a first embodiment of a chamber according to my invention for treatment of cells in an electric field.
Figure 2:
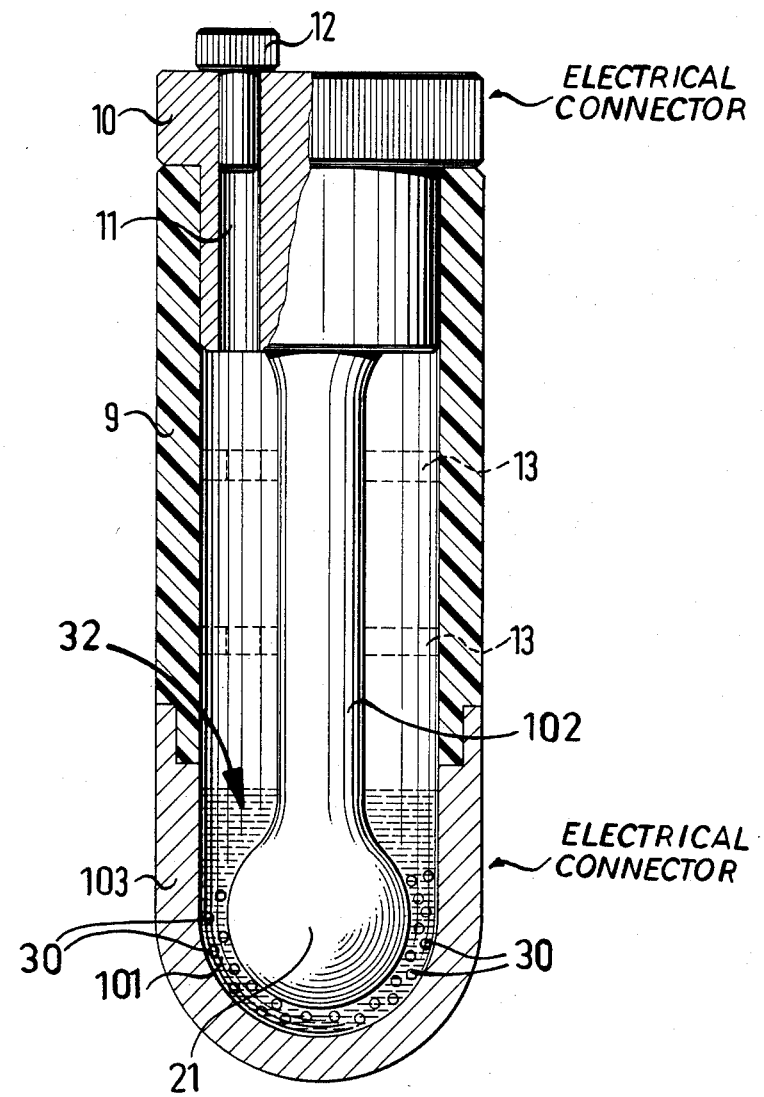
FIG. 2 is a vertical cross sectional view of a second embodiment of a chamber for treatment of cells in an electric field according to my invention.

All embodiments of my chamber shown in the drawing have, as is apparent from FIGS. 1 and 2, a region or inner space 1, 101 which (until an inlet or outlet is reached) is bounded by the coaxially or concentrically positioned surfaces of electrodes 2 and 3 or 102, 103.

In the first embodiment of my chamber shown in FIG. 1 the inner electrode 2 is a cylindrical body in the vicinity of region 1 and is surrounded by an outer electrode 3 so that the region 1 is a cylindrical annular shaped space. This ring shaped space is open on its exteriorly directed front end and has an outlet 4 there. At the other end of the region 1 there is a radial transverse hole 5 in the inner electrode 2 which opens into an axial duct 6 positioned in the inner electrode 1. This duct 6 is connected to a conical passage 7 connected to the outside which widens in the direction of the exterior whose dimensions are so chosen that a pipette can be inserted.

The inner electrode 2 and the outer electrode 3 are separated from each other by an insulating member 8. The outer electrode 3 is accessible from the exterior near region 1 and inner electrode 2 in the upper region of the chamber. The outer electrode is moreover conical and tapered toward its bottom. The chamber can be designed for the voltages required for performing the electrical treatment of the cells or the like biological materials while it is mounted in a socket connector corresponding to the shape of the chamber.

An exact quantity or dose of a solution in which the cells are suspended can be fed into region 1 by a pipette. By filling the chamber with an exact quantity of an additional solution the treated cell suspension can be forced out of the bottom of the chamber through outlet 4 for example into a test tube.

In one example of my chamber region 1 has the following dimensions: outside diameter D=4.4 mm, inside diameter d =4.0 mm and a height of 12 mm. Thus the region volume is 32 microliters. The electrode spacing is 0.2 mm.

In the second embodiment of the chamber shown in FIG. 2 the inner electrode 102 is rod shaped with a ball or spherical shaped end 21. The outer casing of the chamber has the shape of a test tube, whose bottom portion comprises the outer electrode 103 and whose top cylindrical portion 9 is made from plastic.

A cap 10 composed of metal is connected to the rod shaped portion of the inner electrode 102. The cap 10 has an opening 11 with a stopper 12 in it. For guiding the inner electrode 102 in the cylindrical portion 9 of the test tube shaped outer casing guide rings 13 are provided.

In order to provide the electrical treatment of the cells 30 in the suspension 32 in region 101 a voltage is applied to the outer electrode 103 and the inner electrode 102 through the cap 10.

In this example the outer diameter of the ball shaped end 21 is 19.6 mm and the inner diameter of the outer electrode 103 is 20 mm resulting in a region volume of about 250 microliters and thus a clearance of 0.20 mm.

In preparation for the electrical treatment of the cells 30 in a chamber of the above given dimensions approximately 250 microliters of solution and after that 10 to 200 microliters of cell suspension are put into the chamber through the opening 11. After the cells 30 arrive in region 101 by sedimentation the chamber is connected for the required time to a source of electricity. Subsequently the inner electrode 102 is removed from the outer casing and the solution found therein can be subsequently processed.

Figure 3:
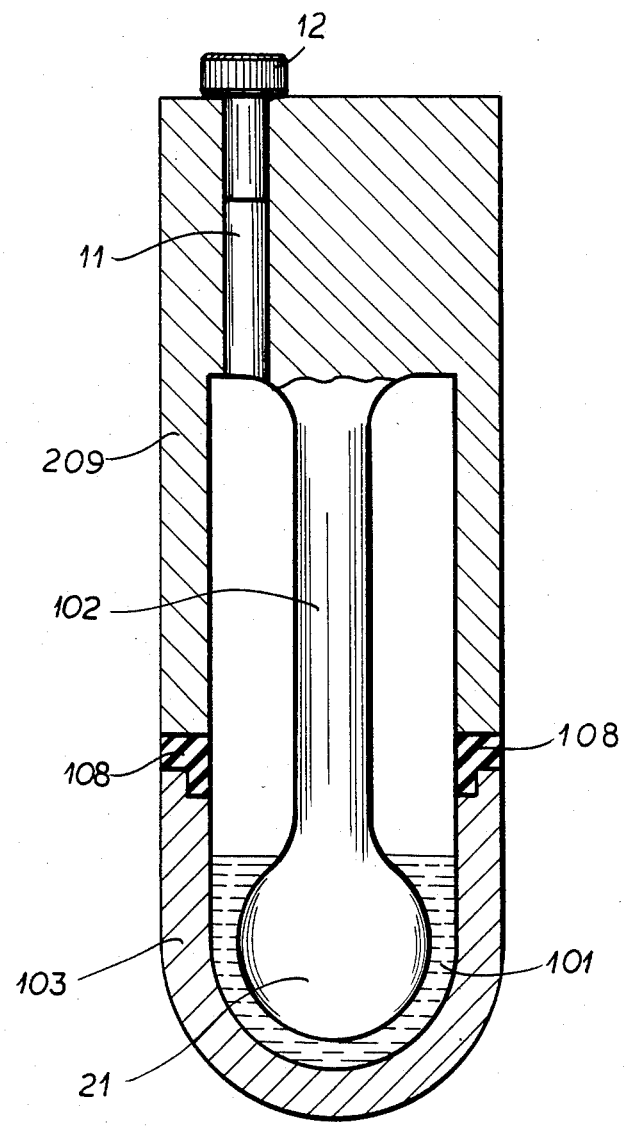
FIG. 3 is a vertical cross sectional view of a third embodiment of a chamber for treatment of cells in an electric field according to my invention.

In FIG. 3 a third embodiment of my chamber for treatment of cells with an electric field is shown which is identical with the second embodiment except that the top portion of the outer casing above the outer electrode 103 consists of a cylindrical upper part 209 of the inner electrode 202 which is spaced from the outer electrode 103 by the ring shaped insulating body 108.

Figure 4:
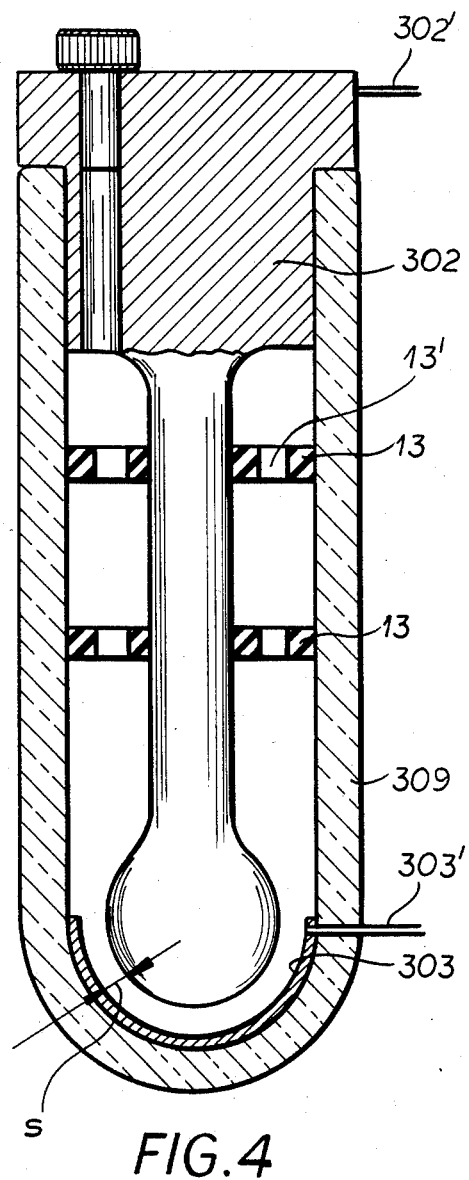
FIG. 4 is a section through another cell treatment device.

FIG. 4 shows an embodiment generally similar to FIG. 2 but wherein the glass test tube 309 has a coating 303 providing the outer electrode. The conductors 302' of the inner electrode and 303' of the outer electrode 303 have also been shown. The gap between the electrodes is shown to have a uniform width s and the guide disks 13 with their holes 13' are also visible here.

I claim:

1. In an apparatus for treatment of cells in an electric field comprising two electrodes which have a constant spacing from each other in the vicinity of a region of an interior space of said apparatus for containing a suspension of said cells accessible from the exterior of said apparatus, the improvement wherein said electrodes consist of an inner one of said electrodes and an outer one of said electrodes mounted exteriorly to said inner one and said outer one of said electrodes at least partially encloses said inner one of said electrodes so that the walls of said region form the opposing surfaces of said electrodes and are equidistant from each other and said inner electrode is spaced from said outer electrode, above which a portion of said inner electrode extends accessible from the exterior, by an insulating member separating said electrodes from each other, said inner electrode and the inside of said outer electrode having substantially cylindrical surfaces in said vicinity of said region so that said region is a substantially cylindrical annular space, and a front end of said cylindrical space being open to the exterior and at least one radial transverse passage in said inner electrode connects to the opposing rear end of said cylindrical space and opens into an axial duct which is formed in said inner electrode and which opens into an inlet in said portion of said inner electrode accessible from said exterior.

2. The improvement defined in claim 1 wherein said axial duct opens into a conical passage widening toward said exterior whose dimensions are so selected that a standard pipette can be inserted therein.

3. The improvement defined in claim 2 wherein said front end of said outer electrode is conically tapered.

4. In an apparatus for treatment of cells in an electric field comprising two electrodes which have a constant spacing from each other in the vicinity of a region of an interior space of said apparatus for containing a suspension of said cells accessible from the exterior of said apparatus, the improvement wherein said electrodes consist of an inner one of said electrodes and an outer one of said electrodes mounted exteriorly to said inner one and said outer one of said electrodes at least partially encloses said inner one of said electrodes so that the walls of said region form the opposing surfaces of said electrodes and are equidistant from each other and said inner electrode is spaced from said outer electrode, above which a portion of said inner electrode extends accessible from the exterior, by an insulating member separating said electrodes from each other, the surface of said inner electrode being approximately ball shaped in said vicinity of said region and said outer electrode having an inside surface aooroximately conforming to said approximately ball shaped surface of said inner electrode so that said region is positioned between and partially bounded by two concentric ones of said approximately ball shaped surfaces, and said inner electrode is rod shaped and has a ball shaped end.

5. The improvement defined in claim 4 wherein said inner electrode projects into an outer casing shaped like a test tube, wherein in said vicinity of said region the inner surface of said outer casing is simultaneously the inner surface of said outer electrode.

6. The improvement defined in claim 5 wherein a plurality of guide rings are provided for said inner electrode on the inside of said outer casing.

7. The improvement defined in claim 6 wherein said outer casing is formed by said outer electrode in said vicinity of said region.

8. The improvement defined in claim 7 wherein the remaining portion of said outer casing is said insulating member.

9. The improvement defined in claim 7 wherein said outer electrode is separated from the remaining portion of said outer casing by said insulating member.

10. The improvement defined in claim 9 wherein the portion of said inner electrode accessible from said exterior opposite to said ball shaped end of said inner electrode has a cap for said outer casing formed like a test tube.

11. The improvement defined in claim 10 wherein said cap has an opening with a stopper.

12. An apparatus for treatment of cells from living matter with an electric field comprising:

an inner and an outer electrode having a constant spacing from each other and defining an interior space of said apparatus for containing a suspension of said cells accessible from the exterior of said apparatus, said outer electrode at least partially enclosing said inner electrode so that the walls of said region forming the opposing surfaces of said electrodes are equidistant from each other; and an insulating member separating said electrodes from each other and spacing said inner electrode from said outer electrode, above which said inner electrode extends in a portion accessible from said exterior, and wherein:

substantially cylindrical surfaces are provided on said inner electrode and the inside of said outer electrode in said vicinity of said region so that said region is a substantially cylindrical annular space;

an outlet at the front end of said cylindrical space opens to said exterior;

at least one radial transverse passage in said inner electrode is connected to the opposing rear end of said cylindrical space;

a conical passage in said inner electrode widens toward and opens into said exterior whose dimensions are so selected that a standard pipette can be inserted therein; and an axial duct is provided in said inner electrode and which connects said conical passage and said radial transverse passage to each other.

13. The apparatus defined in claim 12 wherein said space is dimensioned so as to retain said suspension therein by capillary action.

14. The apparatus defined in claim 12 wherein said space is provided with a passage opening to the exterior and dimensioned so as to retain said suspension in said space by capillary action.

15. The apparatus defined in claim 12 wherein said passage is formed by capillary channels.

* * * * *